(12) United States Patent
Sawahata et al.

(10) Patent No.: US 6,855,931 B2
(45) Date of Patent: Feb. 15, 2005

(54) SCANNING ELECTRON MICROSCOPE AND SAMPLE OBSERVATION METHOD USING THE SAME

(75) Inventors: Tetsuya Sawahata, Hitachinaka (JP); Mitsugu Sato, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/815,817

(22) Filed: Apr. 2, 2004

(65) Prior Publication Data

US 2004/0183016 A1 Sep. 23, 2004

Related U.S. Application Data

(63) Continuation of application No. 10/406,455, filed on Apr. 4, 2003, now Pat. No. 6,740,877, which is a continuation of application No. 09/656,836, filed on Sep. 7, 2000, now Pat. No. 6,555,816.

(30) Foreign Application Priority Data

Sep. 17, 1999 (JP) ............................................ 11-264129

(51) Int. Cl.[7] ...................... G01N 23/00; G01N 23/225; H01J 37/28
(52) U.S. Cl. ........................ 250/310; 250/306; 250/307; 250/309; 250/311; 250/396 R; 250/397; 250/398; 250/399
(58) Field of Search ................................. 250/306, 307, 250/309–311, 397–399, 396 R; 378/45

(56) References Cited

U.S. PATENT DOCUMENTS

| | | | |
|---|---|---|---|
| 3,812,288 A | 5/1974 | Walsh et al. | |
| 3,813,545 A | 5/1974 | Barnhart et al. | |
| 4,494,000 A | 1/1985 | Shii et al. | |
| 4,520,264 A | 5/1985 | Tsuno et al. | |
| 5,029,019 A | 7/1991 | Yoshihara et al. | |
| 5,044,001 A | 8/1991 | Wang | |
| 5,225,676 A | 7/1993 | Matsuya | |
| 5,362,964 A | 11/1994 | Knowles et al. | |
| 5,659,174 A | 8/1997 | Kaneoka et al. | |
| 5,731,580 A | 3/1998 | Sato et al. | |
| 5,801,382 A | 9/1998 | Noda et al. | |
| 5,903,004 A | * 5/1999 | Koshihara et al. | .......... 250/310 |
| 5,936,244 A | 8/1999 | Yajima et al. | |
| 5,939,720 A | 8/1999 | Todokoro | |
| 6,031,230 A | 2/2000 | Toumatsu | |
| 6,072,178 A | 6/2000 | Mizuno | |
| 6,365,897 B1 | 4/2002 | Hamashima et al. | |
| 6,555,816 B1 * | 4/2003 | Sawahata et al. | .......... 250/310 |
| 6,740,877 B2 * | 5/2004 | Sawahata et al. | .......... 250/310 |

FOREIGN PATENT DOCUMENTS

| | | |
|---|---|---|
| JP | 8-124512 | 5/1996 |
| JP | 8-279345 | 10/1996 |
| JP | 11-135052 | 5/1999 |

\* cited by examiner

*Primary Examiner*—John R. Lee
*Assistant Examiner*—Bernard E. Souw
(74) *Attorney, Agent, or Firm*—McDermott Will & Emery LLP

(57) ABSTRACT

According to the present invention, there are newly provided in a scanning electron microscope with an in-lens system a first low-magnification mode that sets the current of the object lens to be zero or in a weak excitation state, and a second low-magnification mode that sets the current of the object lens to be a value that changes in proportion to the square root of the accelerating voltage. The scanning electron microscope has a configuration wherein normal sample image (secondary electron image) observation is performed in the first low-magnification mode, and it switches the first low-magnification mode to the second low-magnification mode when X-ray analysis is performed. As a result, both sample image (secondary electron image) observation and X-ray analysis can be performed in low-magnification mode.

3 Claims, 6 Drawing Sheets

COURSE OF A REFLECTED ELECTRON IN SECOND LOW-MAGNIFICATION MODE

F I G.1
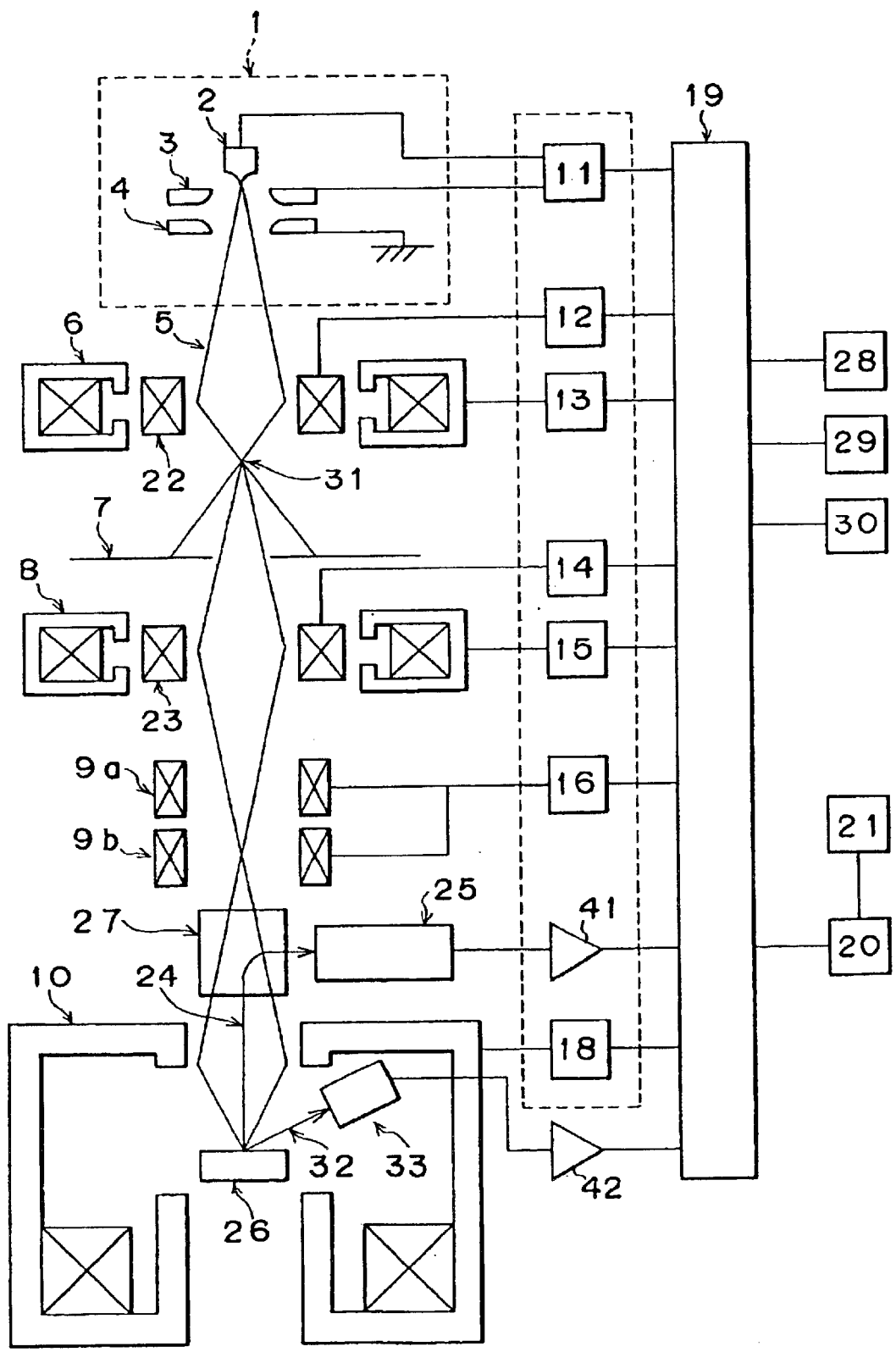

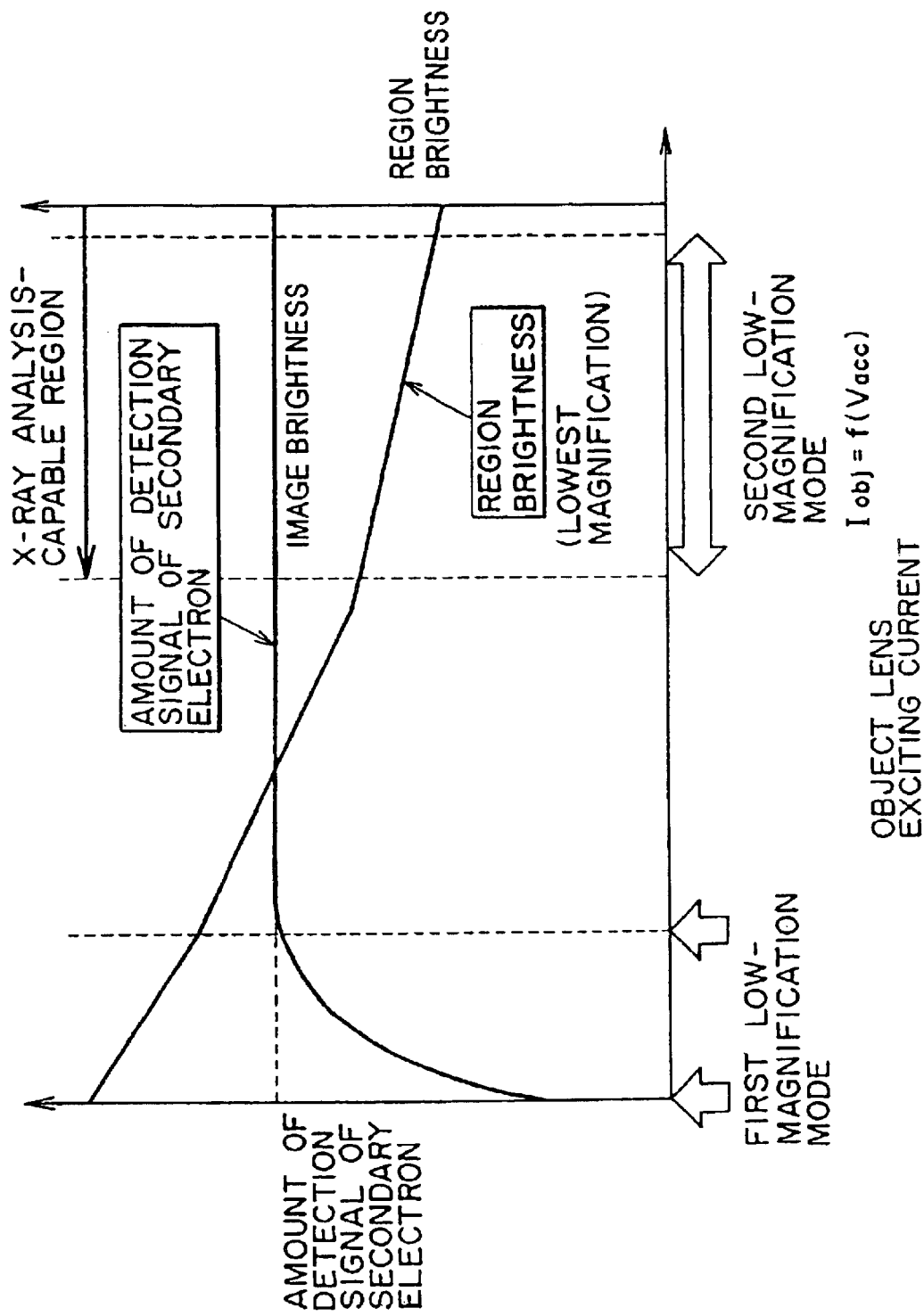

COURSE OF A REFLECTED ELECTRON IN SECOND LOW-MAGNIFICATION MODE

COURSE OF A REFLECTED ELECTRON IN FIRST LOW-MAGNIFICATION MODE

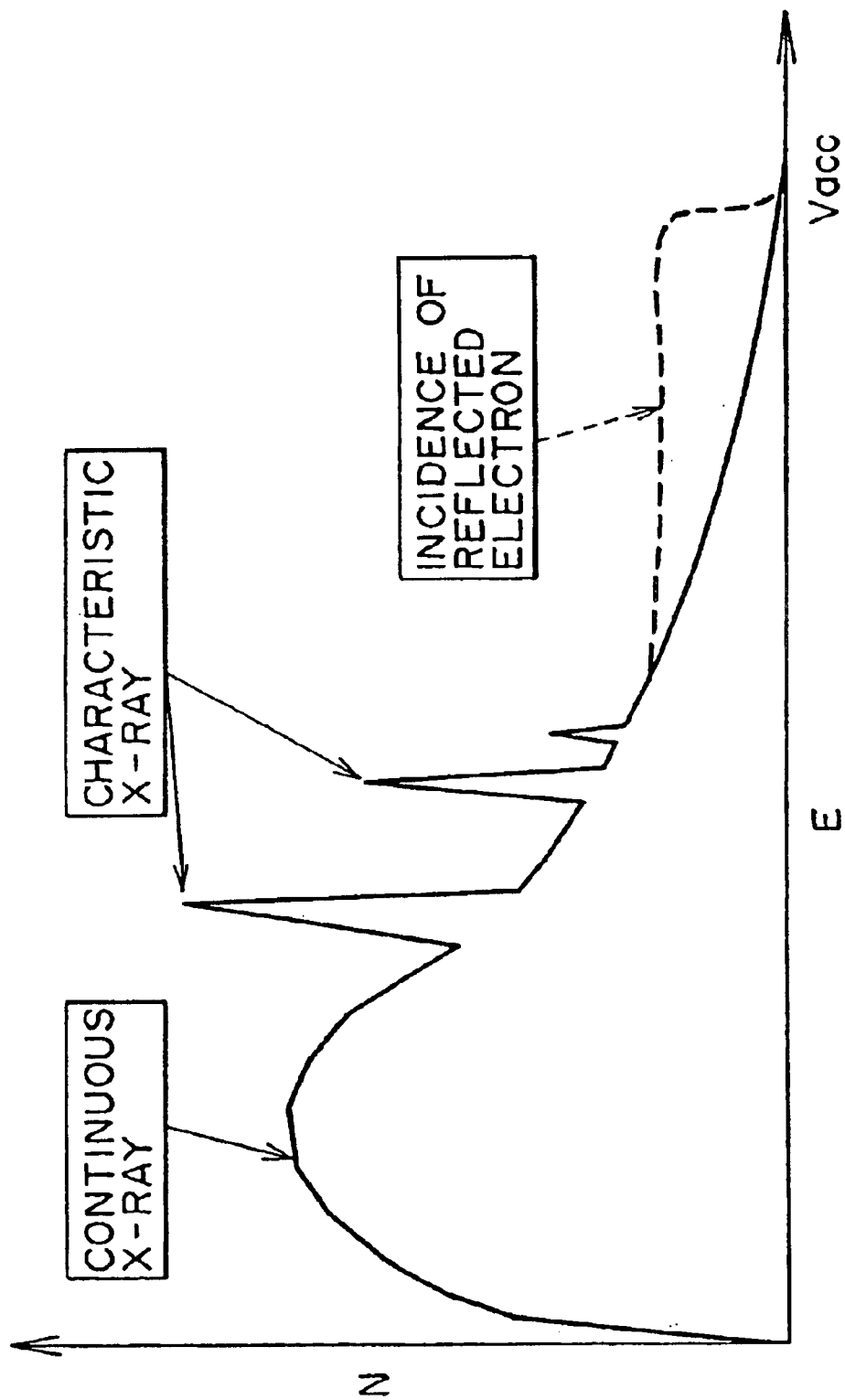

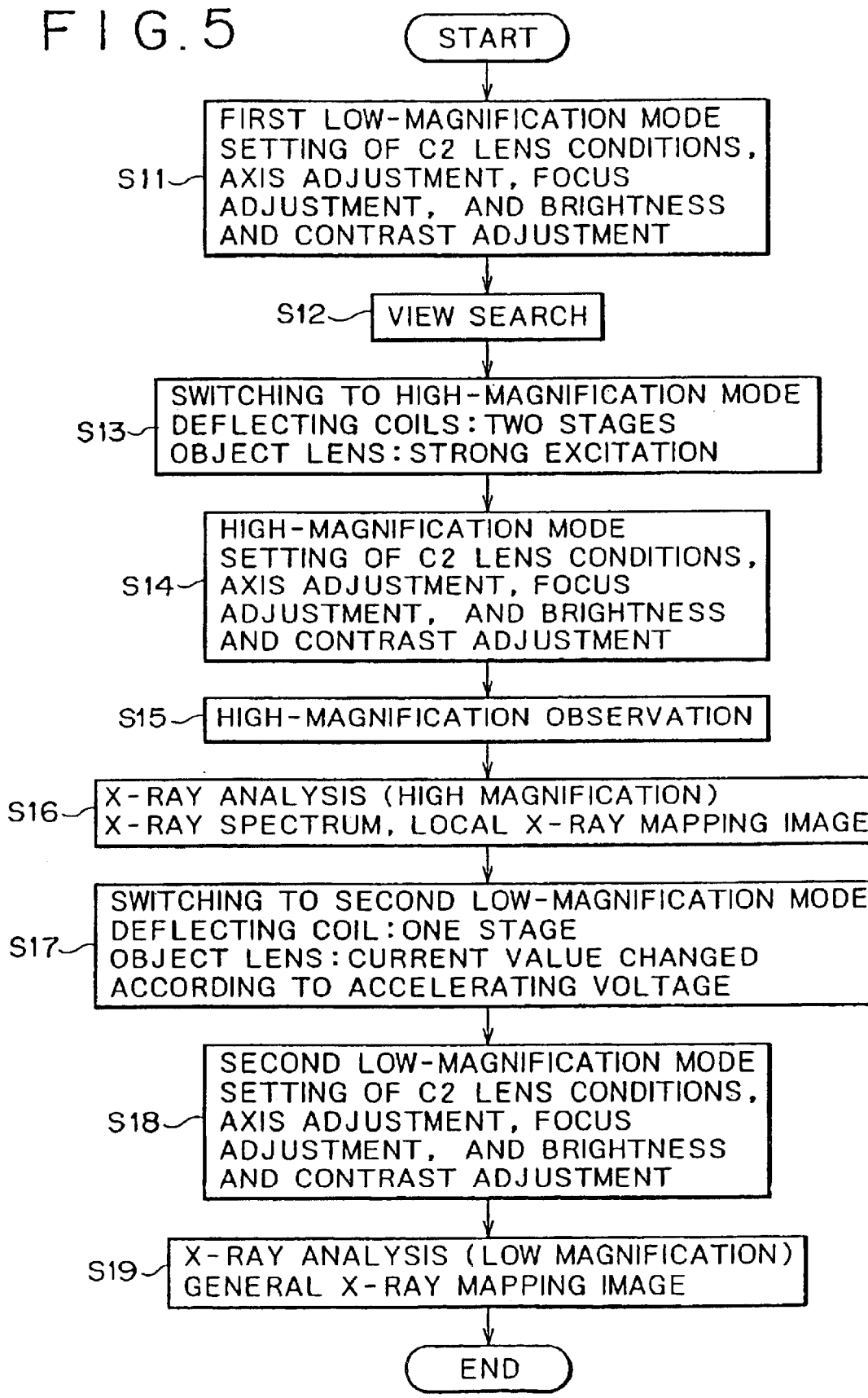

SCANNING ELECTRON MICROSCOPE AND SAMPLE OBSERVATION METHOD USING THE SAME

RELATED APPLICATIONS

This application is a continuation of U.S. patent application Ser. No. 10/406,455, filed Apr. 4, 2003 and entitled "SCANNING ELECTRON MICROSCOPE AND SAMPLE OBSERVATION USING THE SAME," now issued as U.S. Pat. No. 6,740,877, which is a continuation of U.S. patent application Ser. No. 09/656,836, filed Sep. 7, 2000, now U.S. Pat. No. 6,555,816, entitled "SCANNING ELECTRON MICROSCOPE AND SAMPLE OBSERVATION USING THE SAME," both are commonly assigned to the assignee herein.

BACKGROUND OF THE INVENTION

The present invention relates to a scanning electron microscope, and particularly to a scanning electron microscope that allows efficient observation of a magnified sample image (high-magnification image) and a whole sample image (low-magnification image).

In a scanning electron microscope, the object lens is conventionally used at a very short focal distance to obtain scanned images of higher resolution, as is typified, for example, by the in-lens system in which a scanned image is obtained by placing the sample between the magnetic poles of the object lens. When the object lens is used at a short focal distance and sample observation is to be performed under high magnification, there is employed a lens control method for scanning by a primary electron beam wherein deflecting coils for the scanning by the primary electron beam are arranged in two stages along the optical axis, and the deflection point of the primary electron beam is set to be in the proximity of the principal plane of the object lens. The above arrangements are provided in order to prevent distortion caused by the object lens or an increase in the beam diameter of the primary electron beam on the periphery of the scanning region. The lens control method described above is called high-magnification mode. On the other hand, when a view search under low magnification is to be performed at a stage before proceeding to high-magnification observation as described above, or the whole image of the sample is to be observed under low magnification, the following lens control method is employed to enable scanning of a wide region (low-magnification state) by a primary electron beam. That is, the exciting current of the object lens is set to be zero or in a weak excitation state, and the scanning of the sample by a primary electron beam is performed by using a one-stage deflecting coil or two-stage deflecting coils wherein the distance between the deflection point and the surface of the sample is set to be longer than that of high-magnification mode. This lens control method is called low-magnification mode. Thus, observation in a wide magnification range from high to low magnification has been made possible by switching between two magnification modes depending on the observation magnification.

Now, in the X-ray ananlysis of the sample by means of a scanning electron microscope, X-rays occurring from within the scanning range of the primary electron beam (view) are detected to identify the constituent elements of the sample in the view by using an X-ray spectrum and collect information on how the constituent elements are distributed in the view (X-ray mapping image) and the like. An X-ray mapping image, in particular, requires not only local element mapping of the sample through high-magnification observation but also general element mapping of the sample through low-magnification observation.

In the case of X-ray observation by using a scanning electron microscope, if an X-ray detector can be placed in the proximity of the sample, the extraction angle of X-rays can be increased, and therefore highly efficient X-ray analysis is performed. However, if a reflected electron that occurs from the sample by irradiation with the primary electron beam as in the case of X-rays falls on the detection plane of the X-ray detector, it may cause an error or a failure. This problem needs to be avoided.

If the sample is placed within the magnetic field of the object lens, as in the case of the in-lens system, X-ray analysis can be performed in high-magnification mode where the object lens is used in a strongly excited state. This is because the magnetic field of the object lens causes the trajectory of the reflected electron to go away from the detection plane of the X-ray detector. However, in low-magnification mode where the exciting current of the object lens is set to be zero or in a weak excitation state, it is not possible to generate an object lens magnetic field strong enough to cause the trajectory of the reflected electron to go away from the detection plane of the X-ray detector. Therefore X-ray analysis is difficult to perform in this case.

Methods for performing X-ray observation in low-magnification mode include a method in which the X-ray detector is moved so as to keep away from the trajectory of the reflected electron and a method in which a magnet is placed on the detection plane of the X-ray detector to cause the trajectory of the reflected electron to go away from the detection plane of the X-ray detector. However, it is difficult to adopt such methods in the in-lens system because of its structure.

SUMMARY OF THE INVENTION

According to the present invention, low-magnification mode capable of X-ray observation is set in addition to the conventional low-magnification mode suitable for sample image (secondary electron image) observation, and X-ray analysis or particularly X-ray mapping images with a wide view can be obtained by switching between these modes.

According to the present invention, there are provided a first low-magnification mode wherein the current of the object lens is set to be zero or in a weak excitation state, and a second low-magnification mode wherein the current of the object lens is set to be a value that changes in proportion to the square root of the accelerating voltage to be used. A scanning electron microscope according to the present invention is thus provided with a configuration that makes it possible to switch to the first low-magnification mode when normal sample image (secondary electron image) observation is performed and switch to the second low-magnification mode when X-ray analysis is performed.

Specifically, a scanning electron microscope according to embodiments of the present invention comprises an electron source, a first focusing lens for focusing a primary electron beam emitted from the electron source, an object lens diaphragm for removing an unnecessary region of the primary electron beam focused by the first focusing lens, a second focusing lens for focusing the primary electron beam that has passed through the object lens diaphragm, an object lens for focusing the primary electron beam focused by the second focusing lens on a sample, a deflecting means for the scanning of the sample by the primary electron beam, a secondary electron detector for detecting a secondary electron emitted from the sample due to electron beam irradiation, and an X-ray detector for detecting an X-ray emitted from the sample. The scanning electron microscope has functions of focusing the primary electron beam on the sample by using the object lens when the magnification of an image to be scanned is higher than a preset value (high-magnification mode), and focusing the primary electron beam on the sample by using the second focusing lens when the magnification of an image to be scanned is lower than a preset value (low-magnification mode. The scanning electron microscope also has a configuration that, in low-magnification mode, makes it possible to switch to a first low-magnification mode in which the exciting current of the object lens is set to be a constant value independently of the accelerating voltage of the primary electron beam, and switch to a second low-magnification mode in which the exciting current of the object lens is changed as a function of the accelerating voltage of the primary electron beam.

The object lens diaphragm limits the focusing angle (aperture) of the primary electron beam on the sample. In addition, the control of the probe current is performed through the control of the focusing conditions of the first focusing lens. The first focusing lens or the second focusing lens may be formed by a lens in one stage or lenses in a plurality of stages.

The sample is placed in the magnetic field of the object lens. For this kind of object lens, there is known a type of object lens called an in-lens or a type of object lens called a snorkel lens.

The first low-magnification mode sets the exciting current of the object lens to be zero or in a weak excitation state. In other words, the first low-magnification mode sets the exciting current of the object lens to be the minimum exciting current of the object lens that does not lower the efficiency of secondary electron detection, or the exciting current of the object lens that provides the maximum view for the observation magnification. The exciting current of the object lens in the second low-magnification mode is set to be a value in proportion to the square root of the accelerating voltage of the primary electron beam.

The first low-magnification mode and the second low-magnification mode can be configured in such a way that switching between the first low-magnification mode and the second low-magnification mode is performed automatically according to the set value of magnification in low-magnification observation. In the first low-magnification mode, the exciting current of the object lens is lower than that of the second low-magnification mode, and the brightness region is wider than that of the second low-magnification mode (Observation under lower magnification is possible). Therefore, the range of observation magnifications is widened by setting a threshold value of observation magnification in the scanning electron microscope in advance so that it switches to the first low-magnification mode if a desired observation magnification is lower than the threshold value, and it switches to the second low-magnification mode if a desired observation magnification is higher than the threshold value.

For example, because it is easy to correct the angle of image rotation and X-ray observation is possible, the scanning electron microscope can be used in such a manner that it selects the second low-magnification mode when normal low-magnification observation is performed, and it automatically switches to the first low-magnification mode if observation is to be performed under lower magnification.

In addition, it is desirable to have the scanning electron microscope configured in such a manner that it has storage means that each stores setting values of brightness and contrast of the sample image independently for the high-magnification mode, the first low-magnification mode, and the second low-magnification mode, and according to switching to each of the magnification modes, the setting values of brightness and contrast for each of the magnification modes are automatically set to be the values stored in the storage means.

It is desirable that the deflecting means have a function of controlling the scanning direction of the primary electron beam, and the scanning direction of the primary electron beam be controlled according to switching between high-magnification mode, the first low-magnification mode, and the second low-magnification mode. It is desirable that the control of the scanning direction of the primary electron beam by the deflecting means be performed in such a way that the scanning direction of the primary electron beam on the sample substantially corresponds to the X direction of the sample stage.

When sample observation is to be performed by using the scanning electron microscope disclosed in the embodiments of the present invention, the setting value of the exciting current of the object lens in the first low-magnification mode is usually set to be a value for weak excitation, and the value is switched to zero when the scanned image of the sample is to be recorded. The scanned image of the sample is recorded by taking an image shown on a display, storing or outputting the scanned image of the sample as a file.

In addition, when sample observation is to be performed, observation of an X-ray mapping image in low-magnification mode is performed in the second low-magnification mode.

A scanning electron microscope disclosed in embodiments of the present invention comprises an electron source, a first focusing lens for focusing a primary electron beam emitted from the electron source, an object lens diaphragm for removing an unnecessary region of the primary electron beam focused by the first focusing lens, a second focusing lens for focusing the primary electron beam that has passed through the object lens diaphragm, an object lens for generating a magnetic field at the position of a sample and for focusing the primary electron beam focused by the second focusing lens on the sample, an electron beam deflecting means for the scanning of the sample by the primary electron beam, and an X-ray detector for detecting an X-ray emitted from the sample due to electron beam irradiation, whereby an X-ray mapping image of the sample is obtained. The primary electron beam is focused on the sample by the object lens to perform scanning when the magnification of an image to be scanned is higher than a preset value, and the primary electron beam is focused on the sample by the second focusing lens to perform scanning when the magnification of an image to be scanned is lower than a preset value. The scanning electron microscope has a configuration that sets the exciting current of the object lens to be in a weak excitation state to prevent the incidence of a reflected electron from the sample on the X-ray detector.

Here, if the magnification of an image to be scanned is lower than the preset value, the exciting current of the object lens is changed in proportion to the square root of the accelerating voltage of the primary electron beam.

BRIEF DESCRIPTION OF THE DRAWINGS

FIG. 1 is a schematic view of an example of a scanning electron microscope according to the present invention.

FIG. 2 shows a relation between an object lens exciting current and secondary electron detection efficiency/brightness region in low-magnification mode.

FIG. 4 is a diagram of assistance in explaining the X-ray spectrum detected by an X-ray detector when reflected electrons fall on the X-ray detector.

FIG. 5 is a flowchart showing an example of a process for X-ray analysis.

DETAILED DESCRIPTION OF THE PREFERRED EMBODIMENTS

Figure 3A:
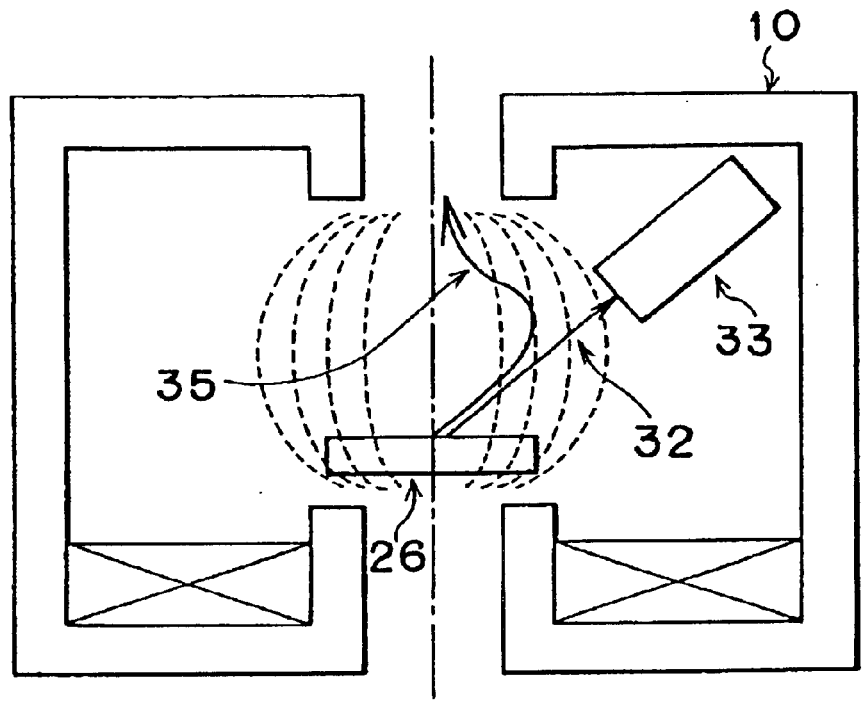
FIGS. 3A and 3B are diagrams of assistance in explaining the presence and the absence of an object lens magnetic field and the trajectories of reflected electrons.

Preferred embodiments of the present invention will now be described.

FIG. 1 is a schematic view of an example of a scanning electron microscope according to the present invention. An extracting voltage is applied between a cathode 2 and a first anode 3 located in an electron source 1 by a high-voltage control power supply 11, so that a primary electron beam 5 is emitted from the cathode 2. The primary electron beam 5 is accelerated by the voltage applied between the cathode 2 and a second anode 4 by the high-voltage control power supply 11 and proceeds to a lens system in the next stage. The primary electron beam 5 is then focused by a first focusing lens 6 (C1 lens) fed by a lens control power supply 13, and passes through an object lens diaphragm 7, whereby an unnecessary region of the beam is removed.

The primary electron beam 5 that has passed through the object lens diaphragm 7 is focused by a second focusing lens 8 (C2 lens) fed by a lens control power supply 15, and is then focused on a sample 26 by an object lens 10 driven by an object lens driving power supply 18. Deflecting coils 9a and 9b, which are driven by a scanning power supply 16, are arranged in two stages between the C2 lens 8 and the object lens 10. The deflecting coils 9a and 9b allow the primary electron beam 5 to scan the sample 26 in a two-dimensional manner.

A beam alignment coil 22, which is driven by a beam alignment coil control power supply 12, is a coil for magnetically correcting the trajectory of the primary electron beam (adjusting the optical axis of the primary electron beam), while an astigmatic coil 23, which is driven by an astigmatic coil control power supply 14, is a coil for magnetically correcting image distortion due to astigmatism.

A secondary electron 24 generated from the sample 26 passes through the object lens 10. Then the secondary electron 24 is deflected to the secondary electron detector side by an orthogonal electromagnetic field generator 27 placed above the object lens, and is detected by a secondary electron detector 25. In the orthogonal electromagnetic field generator 27, there is created a field where the optical axis, the electric field, and the magnetic field are made orthogonal to each other, and the intensities of the electric field and the magnetic field are set in such a manner that the electromagnetic field does not produce the deflection effect on the primary electron beam, whereas the electromagnetic field deflects the secondary electron 24, which proceeds in the direction opposite to the direction of the primary electron beam 5, toward the secondary electron detector 25.

The detection signal of the secondary electron detector 25 is amplified by a signal amplifier 41, is processed by a signal processing means 20, and is displayed on a CRT 21 as a sample image, while if necessary, the detection signal of the secondary electron detector 25 is stored in an image memory 28 as an image signal.

In normal high-resolution observation (high-magnification mode), the primary electron beam 5 is focused on the sample by the object lens 10 in the manner as described above. However, in high-resolution observation conditions involving a short distance between the object lens 10 and the sample 26, in particular, the distance from the deflection point to the sample 26 is also shortened, and therefore the maximum observation view (scanning region) to be obtained in high-magnification mode cannot be widened. Thus, to further widen the observation view, the scanning region on the sample 26 is enlarged by switching to the scanning by means of a one-stage deflecting coil.

In this case, if the object lens 10 is strongly excited, as in high-magnification mode, the displayed image is greatly distorted due to lens aberration. Therefore, the primary electron beam 5 is focused on the sample by putting the object lens 10 into a zero excitation state or a weakly excited state and by using the C2 lens 8 (first low-magnification mode).

In X-ray analysis, X-rays 32 generated from the sample 26 fall on the detection plane of an X-ray detector 33 placed in the proximity of the sample, and the detection signal of the X-ray detector 33 is amplified by a signal amplifier 42, is processed by the signal processing means 20, and is displayed on the CRT 21 as an X-ray spectrum and an X-ray mapping image.

In normal high-resolution observation, lens control is performed in high-magnification mode, as in the case of the observation of a secondary electron image. If X-ray observation is to be performed with a view wider than the maximum observation view obtained in high-magnification mode, the exciting current of the object lens 10 is set to be a value in proportion to the square root of the accelerating voltage, and the primary electron beam 5 is focused on the sample by using the C2 lens 8 (second low-magnification mode).

Each of the power supplies 11 to 18 mentioned above is controlled by a CPU 19. The CPU 19 also controls the signal processing means 20. In addition, the CPU 19 is connected with a memory (storage area) 29 to be used exclusively for high-magnification mode and a memory (storage area) 30 to be used exclusively for low-magnification mode. The memory 29 exclusively for high-magnification mode stores the values of the signal amplifier 41 and the signal processing means 20 that are set with respect to the brightness and the contrast of a sample image when its observation is performed in high-magnification mode. The memory 30 exclusively for low-magnification mode stores the values of the signal amplifier 41 and the signal processing means 20 that are set with respect to the brightness and the contrast of a sample image when its observation is performed in the first low-magnification mode, as well as the values of the signal amplifier 41 and the signal processing means 20 that are set with respect to the brightness and the contrast of a sample image when its observation is performed in the second low-magnification mode.

Figure 3B:
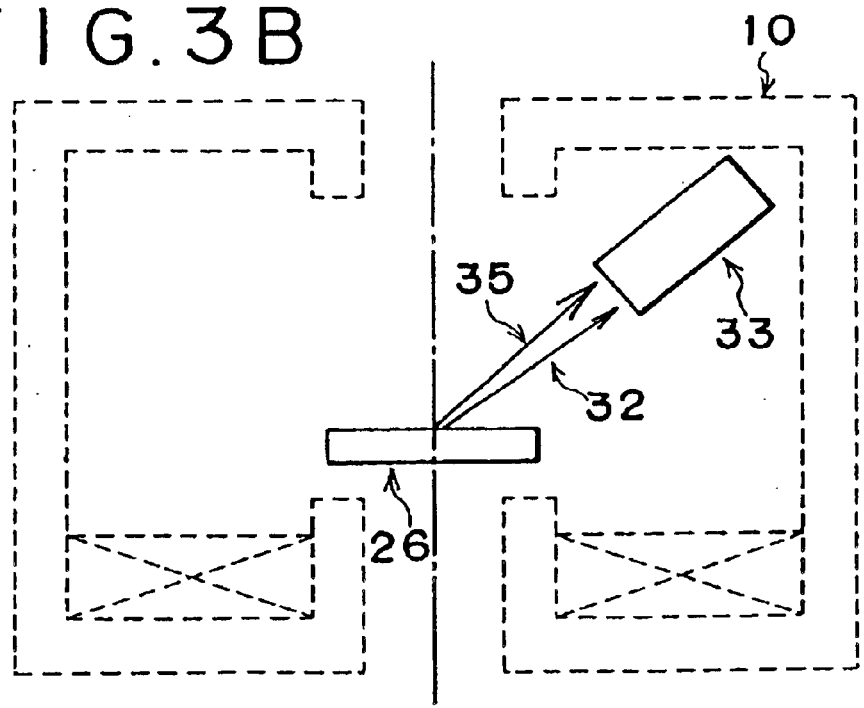

Next, the first low-magnification mode and the second low-magnification mode will be described. FIG. 2 shows a relation between the object lens exciting current and the secondary electron detection efficiency/brightness region in low-magnification mode. FIGS. 3A and 3B show diagrams of assistance in explaining the presence and the absence of an object lens magnetic field and the trajectories of reflected electrons. FIG. 4 shows a diagram of assistance in explaining the X-ray spectrum detected by the X-ray detector when a reflected electron falls on the X-ray detection plane of the X-ray detector.

In general, if the exciting current of the object lens is varied in lens control, the amount of detection signal of a secondary electron and the brightness region of the image is changed in the manners as shown in FIG. 2. The amount of detection signal of a secondary electron represents the brightness of the sample image. As the object lens current is increased, the amount of detection signal increases due to the winding-up effect of the magnetic field of the object lens, resulting in a bright image. However, the amount of detection signal reaches convergence at a certain current value. On the other hand, the brightness region of the image determines the lowest magnification of the image. When the exciting current of the object lens is zero, the widest view and a sample image with no variations in brightness can be obtained. However, as the object lens current is increased, the brightness region of the image is reduced, with the result that the periphery of the image becomes dark.

Therefore, the exciting current value of the object lens in the first low-magnification mode is set to be a value that can maximize the brightness region of the image, chosen from among the current values at which the amount of detection signal of a secondary electron is converged. If the microscope is used specifically for taking sample images or the like, the exciting current value of the object lens is set to be zero so that the brightness region of an image is maximized. The exciting current value of the object lens is set to be zero for the following reason. When the exciting current value of the object lens is zero, the amount of detection signal of a secondary electron is small, but if the microscope is used only for taking sample images, the small amount of detection signal of a secondary electron can be compensated for by setting the exposure time or the signal accumulation time to be long.

On the other hand, the second low-magnification mode is the low-magnification mode for X-ray analysis, and the current value in the second low-magnification mode is changed within the range of current values that are higher than the exciting current value of the object lens set in the first low-magnification mode. In X-ray analysis, an object lens magnetic field needs to be generated according to the energy of a reflected electron (=accelerating voltage) to make the trajectory of the reflected electron go away from the detection plane of the X-ray detector. Therefore the current value is set in proportion to the square root of the accelerating voltage.

In normal low-magnification mode (the first low-magnification mode), the magnetic field of the object lens 10 is not present or weak, as shown in FIG. 3B, and therefore the reflected electron 35 generated from the sample 26 falls on the detection plane of the X-ray detector 33. The X-ray spectrum detected by the X-ray detector 33 in this case is such as is shown in FIG. 4. It is difficult to perform X-ray analysis in this case because the reflected electron 35 incident on the detection plane of the X-ray detector 33 causes a detection error or a failure. Therefore, in the low-magnification mode for X-ray analysis, the exciting current value of the object lens is set in such a way that the reflected electron 35 goes away from the detection plane of the X-ray detector 33 and the brightness region of the image is secured by setting the above value to be the lowest current value, as shown in FIG. 3A. The higher the accelerating voltage of the primary electron beam is, the greater the exciting current of the object lens needs to be, and therefore the brightness region of the image is reduced in response thereto.

Moreover, in normal observation of a secondary electron image by means of the scanning electron microscope, the accelerating voltage during the observation of the same sample is constant in many cases, while during X-ray observation, the accelerating voltage needs to be changed to perform X-ray observation. The accelerating voltage needs to be changed for the following reason. Of the elements that form the sample, light elements emit X-rays by irradiating with a primary electron beam accelerated to a low velocity, while heavy elements require irradiation with a primary electron beam accelerated to a high velocity. Thus, even when the same sample is to be observed, the accelerating voltage of the primary electron beam needs to be changed during its observation, depending on the elements to which attention is directed.

The primary electron beam proceeds in a spiral trajectory in the magnetic field of the object lens to be focused on the sample. If the accelerating voltage is changed or the exciting current is changed here, the trajectory of the primary electron beam is changed, thereby resulting in a rotation of the image. However, if excitation $IN/\sqrt{V}$ (I: exciting current, N: number of coil turns, V: accelerating voltage) is held constant, the trajectory of the primary electron beam is not changed, and therefore the rotation of the image can be readily controlled. Since the number of coil turns N is a constant value specific to the object lens, the excitation can be held constant at all times by changing the exciting current I in proportion to the square root of the accelerating voltage V. Similarly, the magnification of the image can be readily controlled by changing the current of the deflecting coil for scanning the primary electron beam in proportion to the square root of the accelerating voltage V.

Here, in brief, supplementary description of the excitation of the object lens will be made. In high-magnification mode, the primary electron beam 5 is controlled by the magnetic field generated by the object lens 10 in such a way that the primary electron beam 5 is focused on the sample 26. In this case, a strong exciting current flows through the object lens 10, enabling short focusing. Therefore high-magnification observation can be performed. Such excitation of the object lens 10 is called strong excitation.

In the first low-magnification mode, the primary electron beam 5 is controlled in such a way that the exciting current of the object lens 10 is set to be zero or weak and the primary electron beam 5 is focused on the sample 26 by the focusing lens (second focusing lens 8) nearest to the object lens 10. This makes it possible to enlarge the brightness region and therefore perform an observation with a wide view (low-magnification observation). In this case, the exciting current flowing through the object lens 10 is lower than that in high-magnification mode, and accordingly it cannot cause the primary electron beam 5 to be focused on the sample. In the second low-magnification mode, the exciting current of the object lens 10 is controlled in such a way that the exciting current changes in proportion to the square root of the accelerating voltage V. The exciting current in the second low-magnification mode is greater than that in the first low-magnification mode but lower than that in high-magnification mode. As in the first low-magnification mode, the object lens 10 cannot cause the primary electron beam 5 to be focused on the sample 26 (weak excitation). In the second low-magnification mode, the incidence of the reflected electron 35 on the X-ray detection plane of the X-ray detector 33 can be restricted by the magnetic field of the object lens generated by an exciting current greater than that of the first low-magnification mode.

FIG. 5 is a flowchart showing an example of the process for X-ray analysis. When sample observation is to be performed, the processing is ready for the first low-magnification mode at a step 11 to perform the setting of C2 lens (second focusing lens) conditions, axis adjustment, focus adjustment, and brightness and contrast adjustment.

The brightness adjustment is performed by setting the value of the signal amplifier 41 for the secondary electron detector 25 to be the value for the first low-magnification mode stored in advance in the memory 30. The contrast adjustment is performed by setting the value of the signal processing means 20 to be the value for the first low-magnification mode stored in advance in the memory 30. Next, at a step 12, a view search is performed under low magnification.

After the observation view is determined, switching to high-magnification mode is performed at a step 13. In high-magnification mode, the deflectors 9a and 9b are used in two stages, and the object lens 10 is used in a strong excitation state. After proceeding to high-magnification mode, the setting of C2 lens conditions, axis adjustment, focus adjustment, and brightness and contrast adjustment are performed at a step 14. The brightness adjustment is performed by setting the value of the signal amplifier 41 for the secondary electron detector 25 to be the value for high-magnification mode stored in advance in the memory 29. The contrast adjustment is performed by setting the value of the signal processing means 20 to be the value for high-magnification mode stored in advance in the memory 29.

After switching to high-magnification mode, the image is observed under high magnification by means of the scanning electron microscope at a step 15. In addition, X-ray analysis under high magnification is performed at a step 16. Specifically, the X-ray spectrum of a local region of the sample and a local X-ray mapping image are observed.

Next, at a step 17, switching to the second low-magnification mode is performed. In the second low-magnification mode, one of the deflectors is used in one stage, and the object lens 10 is used in a weak excitation state in which the exciting current of the object lens 10 is caused to change in proportion to the square root of the accelerating voltage of the primary electron beam 5. After proceeding to the second low-magnification mode, the setting of C2 lens conditions, axis adjustment, focus adjustment, and brightness and contrast adjustment are performed at a step 18. The brightness adjustment is performed by setting the value of the signal amplifier 41 for the secondary electron detector 25 to be the value for the second low-magnification mode stored in advance in the memory 30. The contrast adjustment is performed by setting the value of the signal processing means 20 to be the value for the second low-magnification mode stored in advance in the memory 30.

Next, at a step 19, X-ray analysis under low magnification, that is, observation of the whole X-ray mapping image of the sample is performed. In this second low-magnification mode, the reflected electron generated from the sample is caused to go away from the X-ray detector 33 by the magnetic field of the object lens 10 in a weakly excited state, and therefore does not fall on the X-ray detector 33. Thus, an element mapping image can be observed under low magnification without a failure that may occur in the X-ray detector 33 or without noise included in the detection signal as in the case of a conventional microscope.

Figure 6:
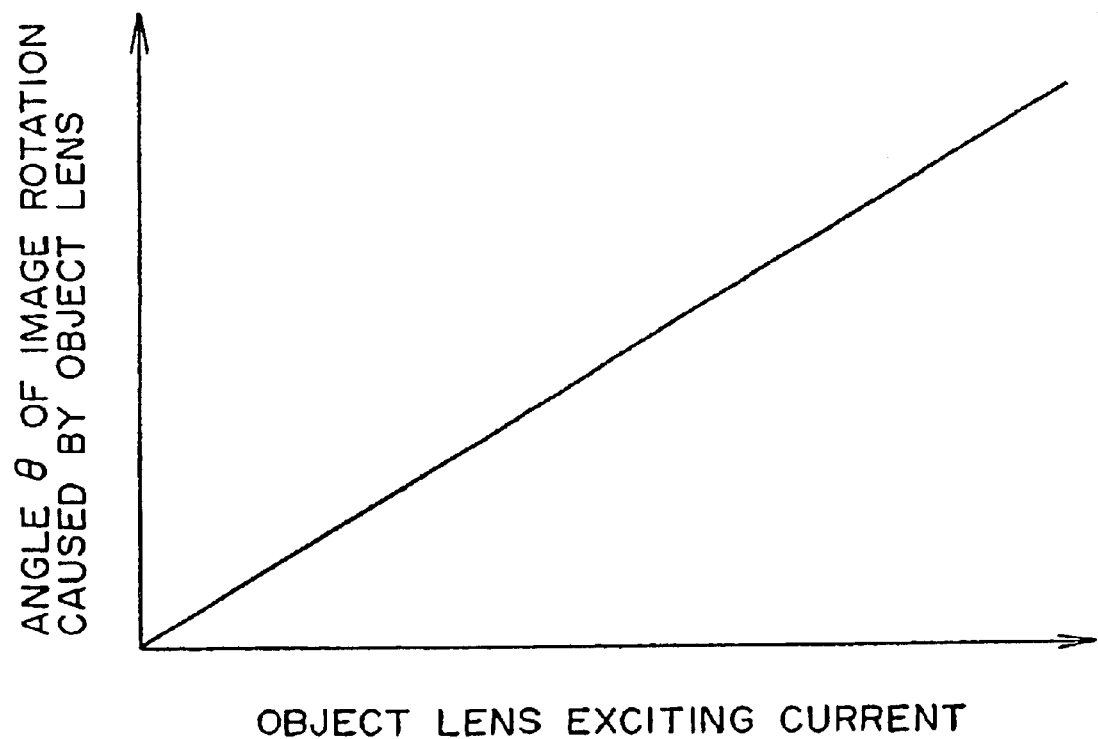
FIG. 6 is a diagram of assistance in explaining image rotation caused by changes in the excitation of an object lens.

Now, if the excitation of the object lens 10 is changed by switching between magnification modes, the rotation effect of the object lens is produced on the scanning direction of the primary electron beam, thereby resulting in a rotated image. FIG. 6 shows a diagram of assistance in explaining the relation between the object lens exciting current and the image rotation. According to the present invention, the scanning direction of the primary electron beam is controlled in such a way that the image rotation caused by the object lens is cancelled in association with the excitation of the object lens, to make the scanning direction of the primary electron beam correspond to the X direction of the sample stage.

In the second low-magnification mode, the microscope is used under the condition of constant excitation (I: exciting current, N: number of coil turns, V: accelerating voltage). Therefore the trajectory of the primary electron beam is not changed in the magnetic field of the object lens, and so the rotation of the image does not occur. Also in high-magnification mode, the rotation of the image will not occur if the microscope is used under the condition of constant excitation. However, if the microscope is used under a condition that the excitation is not held constant, the rotation of the image will occur when the current value of the object lens or the like is changed. In the first low-magnification mode, the microscope is used under the condition that the exciting current of the object lens is held constant, and therefore a rotation of the image will occur when the accelerating voltage of the primary electron beam is changed. Thus, in observation modes where the excitation is not held constant, the scanning direction of the primary electron beam is controlled in such a way that the image rotation caused by the object lens can be cancelled, by adjusting the ratio of the deflecting current flowing through the X deflecting coils of the deflecting coils 9a and 9b to the deflecting current flowing through the Y deflecting coils of the deflecting coils 9a and 9b. As a result, the scanning direction of the primary electron beam on the sample is made to coincide with the X direction of the sample stage at all times.

According to the embodiments of the present invention, efficient low-magnification observation is made possible by setting a plurality of low-magnification modes each suitable for sample image (secondary electron image) observation and for X-ray analysis. The present invention makes it possible to use low-magnification mode during X-ray analysis, in particular, which has previously been difficult, and to obtain an X-ray mapping image with a wide view.

What is claimed is:

1. A scanning electron microscope comprising:

a focusing lens for focusing a primary electron beam on a sample when a low-magnification mode is set;

an objective lens for focusing the primary electron beam on the sample when a high-magnification mode is set;

an X-ray detector for detecting an X-ray emitted from the sample; and a processing unit for controlling the object lens to prevent reflected electrons from entering the X-ray detector when the low-magnification mode is set.

2. A scanning electron microscope having an X-ray detector for detecting an X-ray and a secondary electron detector for detecting secondary electrons, the microscope comprising:

an object lens for generating a magnetic field, wherein the magnetic field is changed automatically in accordance with detection of the X-ray or the secondary electrons, and the magnetic field prevents an incidence of reflected electrons to the X-ray detector when the X-ray is detected.

3. A scanning electron microscope, an X-ray detector for detecting an X-ray and a secondary electron detector for detecting secondary electrons, the microscope comprising:

an objective lens for focusing a primary electron beam or for preventing an incidence of reflected electrons, wherein a parameter related to the object lens is adjusted automatically in accordance with a change of X-ray detection and secondary electron detection.

* * * * *